Figure 1:
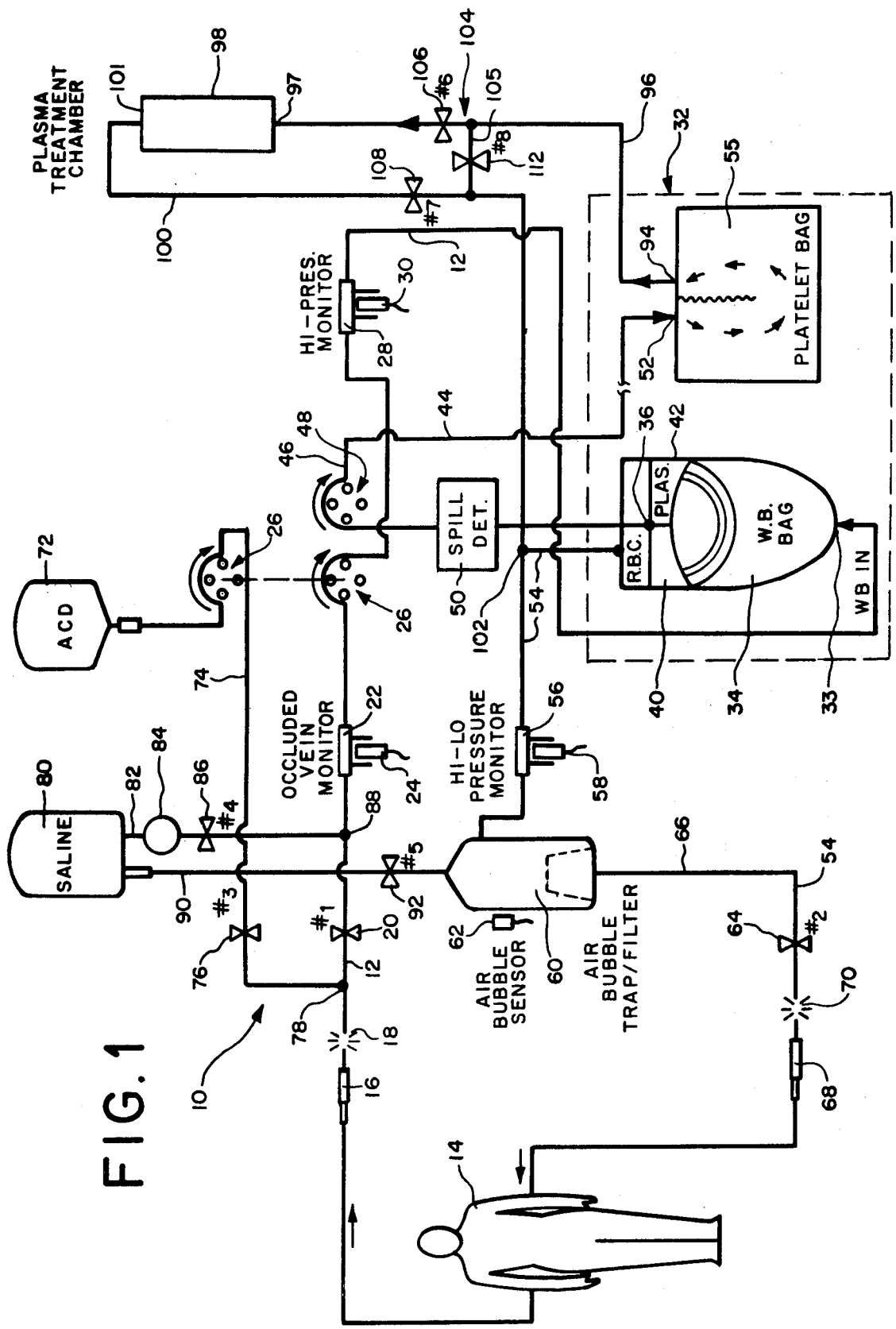

United States Patent [19]

Terman et al.

[11] 4,215,688

[45] Aug. 5, 1980

[54] APPARATUS FOR THE EXTRACORPOREAL TREATMENT OF DISEASE

[75] Inventors: David S. Terman, Houston, Tex.; Michael Sulliva, Buffalo Grove, Ill.; Herbert M. Cullis, Silver Spring, Md.

[73] Assignee: Baxter Travenol Laboratories, Inc., Deerfield, Ill.

[21] Appl. No.: 10,517

[22] Filed: Feb. 9, 1979

[51] Int. Cl.² ............................................. A61M 5/00
[52] U.S. Cl. ........................... 128/214 R; 128/214 D; 210/DIG. 23; 210/24
[58] Field of Search ............... 128/214, 213; 233/1 R; 210/DIG. 23, 22, 23, 24; 422/45

[56] References Cited

U.S. PATENT DOCUMENTS

| | | | |
|---|---|---|---|
| 3,462,361 | 8/1969 | Greenwalt et al. | 210/24 R |
| 4,086,924 | 5/1978 | Latham | 128/214 R |
| 4,103,685 | 8/1978 | Lupien et al. | 128/214 R |
| 4,155,854 | 5/1979 | Marx | 128/214 R |

*Primary Examiner*—Robert W. Michell
*Assistant Examiner*—Thomas J. Wallen
*Attorney, Agent, or Firm*—H. W. Collins; Paul Flattery; Thomas Vigil

[57] ABSTRACT

The apparatus includes a peristaltic pump for withdrawing whole blood from a patient, a device for centrifuging the blood to separate plasma from the whole blood, a plasma treatment chamber for receiving the plasma, a vehicle positioned within the chamber and having an immunoadsorbent agent fixed thereon to interact and bond with an immunological reactant carried by the plasma that is passed through the chamber for removing the immunological reactant from the plasma, tubings connected to recombine the substantially immunological reactant free plasma with the remainder of the whole blood and a peristaltic pump for returning the recombined whole blood to the patient. In one plasma treatment chamber, the vehicle is defined by a spiral coiled membrane which has an immunoadsorbent agent fixed thereon. Each convolution of the spiral is spaced from an adjacent convolution and the coil is positioned within the chamber so that plasma flows through the space between the convolutions of the spiral coiled membrane. Another plasma treatment chamber has a cone therein which establishes different flow rates of plasma through the chamber with the vehicle being defined by particles which have a large surface area, which surround the cone and which have an immunoadsorbent agent bonded thereto.

9 Claims, 9 Drawing Figures

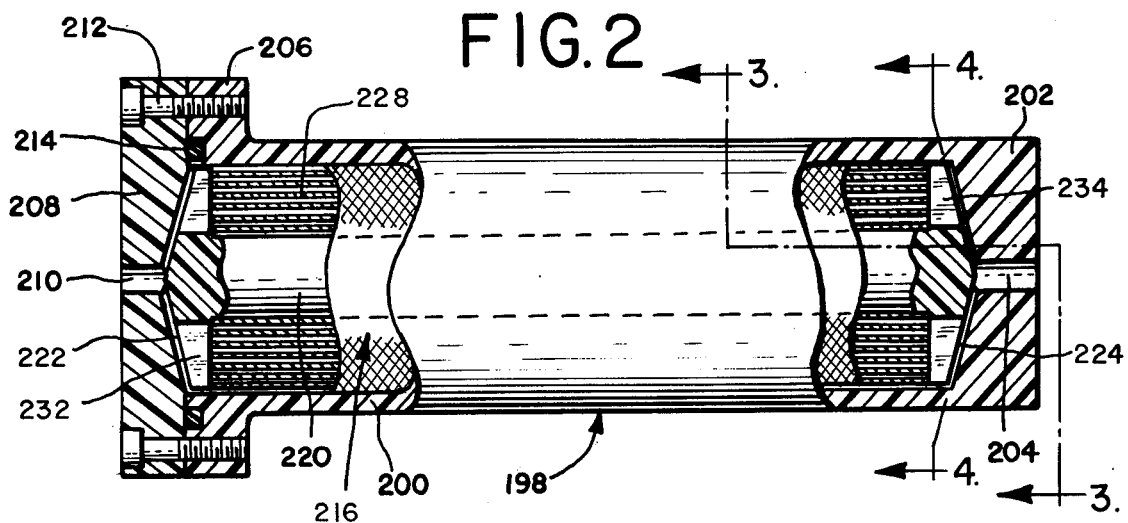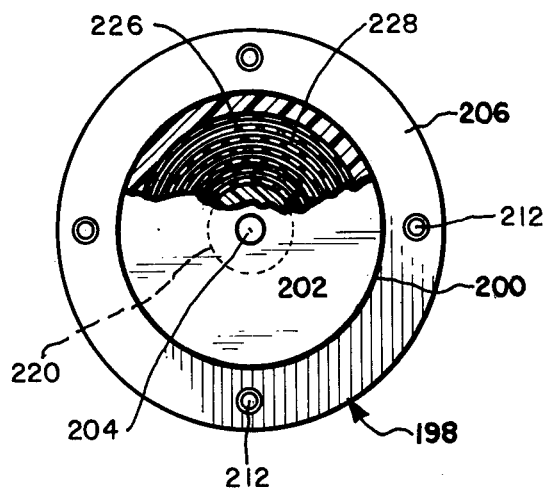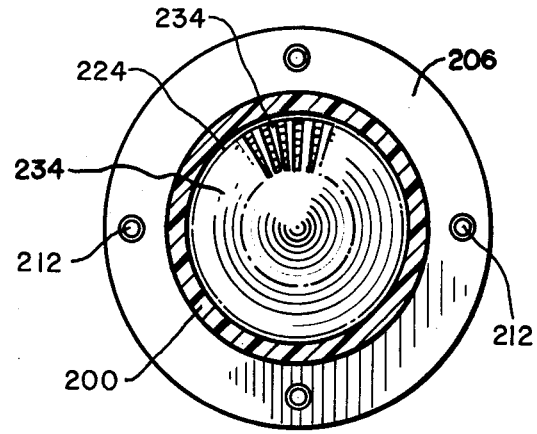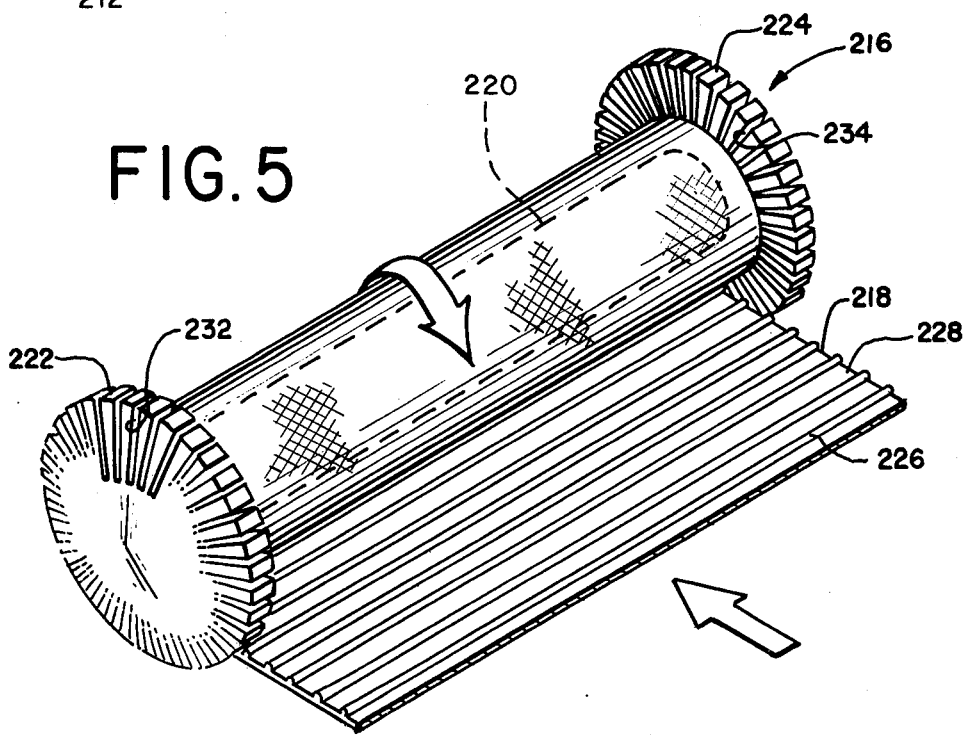

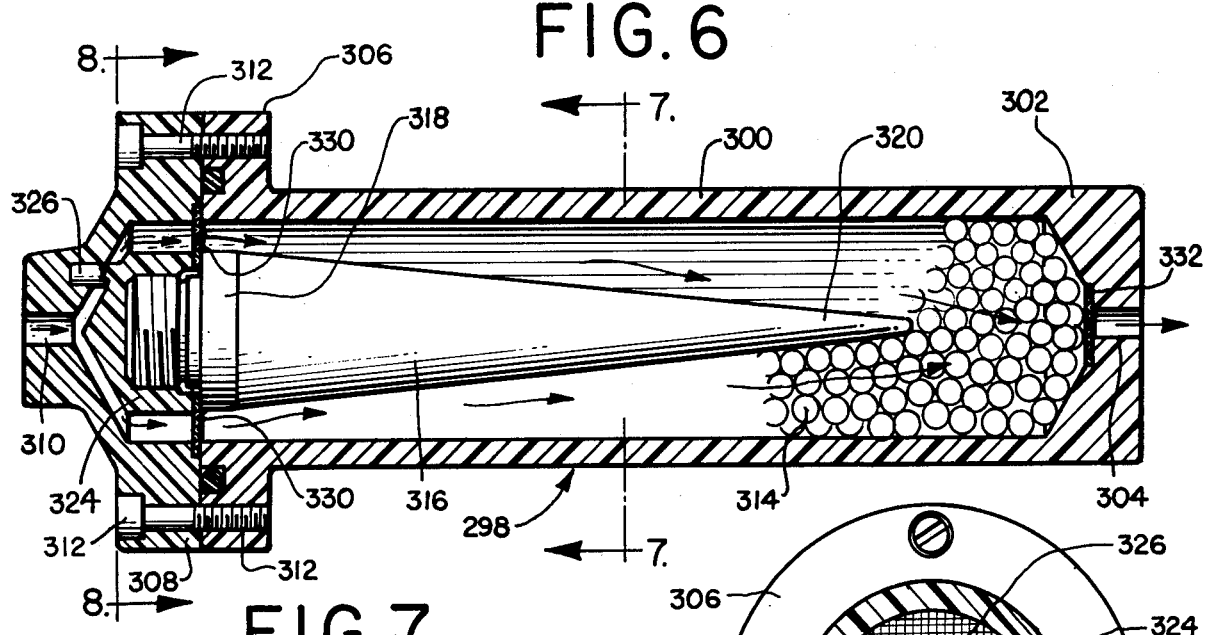
FIG. 6
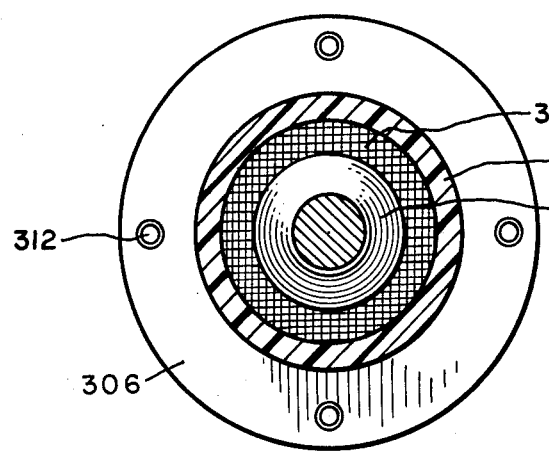
FIG. 7
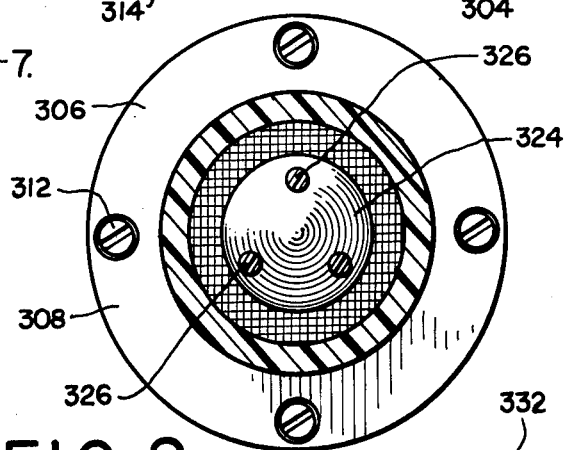
FIG. 8
FIG. 9

APPARATUS FOR THE EXTRACORPOREAL TREATMENT OF DISEASE

BACKGROUND OF THE INVENTION

1. Field of the Invention

The present invention relates to an apparatus for the extracorporeal treatment of disease in which a specific immunological reactant is removed from plasma which has been separated from whole blood and more specifically, to plasma treatment chambers used in the apparatus.

2. Description of the Prior Art

It has been determined that immunological reactants such as antigens, antibodies and antigen-antibody complexes circulating in the blood play an important role in the pathogensis of many diseases. Removal of such pathogenic reactants from blood, and more specifically from the plasma, has been found to be of great therapeutic value.

Systemic lupus erythematosus is one such disease wherein formation of antigen-antibody complexes and deposition of same in tissue causes severe inflammation and removal of such complexes is of therapeutic value.

Also, in resisting and attacking cancerous cells, cytotoxic activity of the body directed to neoplastic cells is blocked by circulating antigens produced by the cancerous cells and interferes with the body's efforts in combatting neoplasia. Here, again, removal of such antigens is of therapeutic value.

Further, the efforts of the body in rejection of tissue transplantation by antibodies circulating in the blood can be alleviated by removal of such antibodies.

Heretofore, various extracorporeal methods and apparatus have been proposed for removing such immunological reactants from plasma.

In practicing such methods for the extracorporeal treatment of disease, whole blood, or plasma only, is circulated through a chamber within which is located a vehicle having thereon an immunoadsorbent agent specific to the immunological reactant to be removed. Typically, the immunoadsorbent agent is an antigen and the immunological reactant is an antibody.

In one apparatus for the extracorporeal treatment of disease, whole blood is removed from a patient into a sterile environment of conduits and chambers. More specifically, the whole blood is withdrawn from the patient by means of a peristaltic pump acting on a tubing which has a needle at one end injected into one arm of the patient. The other end of the tubing is connected to a blood separation chamber in a centrifuge device where the whole blood is centrifuged to segregate and separate the components. Plasma is withdrawn from the separation chamber and passed through a plasma treatment chamber where a specific immunoadsorbent agent on a vehicle, such as a plurality of nylon beads, interacts with a specific immunological reactant in the plasma. Actually, what happens is that the reactant in the plasma attaches itself and becomes bonded to the agent fixed on the vehicle. Substantially reactant free plasma is then withdrawn from the chamber by means of a peristaltic pump, recombined with the other blood components and returned via a tubing and needle to the other arm of the patient.

The extracorporeal treatment of disease has been extensively investigated in connection with the formation of DNA-anti-DNA complexes on a vehicle within a plasma treatment chamber for removing such complexes from the blood. This ability to selectively remove anti-DNA from plasma is a much desired therapeutic measure with respect to systemic lupus erythematosus which is a disease that is at least partially mediated by antibodies to DNA. In this disease, the inflammation caused by deposition of complex formations of anti-DNA antibodies with circulating DNA within tissues is reduced by reason of the extracorporeal treatment of the blood.

In the case of the immunological reactant being an antigen-antibody complex, the treatment consists of two steps. The first step is to pass the plasma through a first chamber having an immunoadsorbent agent which is a specific enzyme whose function is to break down the complex followed by passing the treated plasma through a second chamber having a specific immunoadsorbent agent which forms a complex with part or all of the broken down antigen or antibody.

It is believed that the extracorporeal treatment of disease described above is a major improvement over the presently utilized immunosuppression techniques for treating disease. Present immunosuppression techniques utilize an agent which causes suppression of the overall immune response and which have a wide range of undesirable side effects such as leaving the patient susceptible to various forms of infection from the immunosuppression. Such side effects are not incurred with the extracorporeal treatment of the disease.

Since the immunological reactants are found in the plasma portion of blood, the efficiency of the immunoadsorbent agent can be increased by having only the plasma portion of the blood circulating through the treatment chamber. Also, if whole blood is circulated through the treatment chamber, the efficiency of the immunoadsorbent agent is decreased because particulate matter, such as platelets, etc., can become lodged against and adhere to the coated vehicle thus covering many of the binding sites of the immunoadsorbent agent and preventing their functioning as a filter.

Accordingly the plasma is first separated from the whole blood with a centrifuge device such as that found in the "Celltrifuge" TM machine sold by American Instrument Company, a Division of Travenol Laboratories, Inc. Silver Spring, Md. or such as that found in the "Cell Separator" TM machine sold by Fenwal Division of Travenol Laboratories, Inc. Round Lake, Ill. The "Cell Separator" machine is preferred since it also separates (filters out) platelets from the plasma to provide platelet-poor plasma. This is important since platelets tend to attach themselves to the immunoadsorbent agent and "gum up" the plasma treatment chamber.

Various vehicles have been proposed and the controlling factor in selecting a vehicle is the surface area provided by the vehicle.

Collodion charcoal, nylon microspheres and a collodion membrane have been proposed for use as the vehicle.

To provide a substantial surface area on a membrane, it has also been proposed to provide a spiral coiled membrane and gauze backing. The coil is placed in a cylindrical chamber and plasma percolates axially through the coil. The gauze backing however, limits the flow through the coil and the fibers thereof cover a significant area of the membrane.

Various techniques have been proposed for attaching the immunoadsorbent agent to the vehicle. In one technique, a collodion is sprayed on the vehicle, the particular collodion serving to immobilize and bind the immunoadsorbent agent to the surface of the vehicle.

Another technique for producing the same desired result is to spray cyanogen bromide onto the vehicle, chemically changing the surface of the vehicle, thereby permitting the immunoadsorbent agent to bind to the vehicle surface.

The attachment of the immunoadsorbent agent to the vehicle should be such as to allow no, or only minimal, escape of the immunoadsorbent agent and thus eliminate any possibility of toxicity to the patient's biochemical and hematological status.

As will be described in greater detail hereinafter, the apparatus of the present invention provides improved plasma treatment chambers one of which utilizes a coiled membrane with the convolutions thereof spaced apart to permit plasma to flow freely axially of the membrane through the space between convolutions and another of which is designed in such a manner as to provide different flow rates of plasma through the chamber thereby to cause some turbulence in the plasma flow to enhance contact of immunological reactants with the immunoadsorbent agent on a particulate vehicle.

SUMMARY OF THE INVENTION

According to the invention there is provided in an apparatus for the extracorporeal treatment of disease and of the type comprising means for withdrawing whole blood from a patient, means for separating plasma from the whole blood, means for treating the plasma including a chamber for receiving the plasma and a vehicle positioned within the chamber and having an immuno-adsorbent agent fixed thereon which will interact and bond with an immunological reactant carried by the plasma that is passed through the chamber for removing the immunological reactant from the plasma, and means for recombining the substantially immunological reactant free plasma with the remainder of the whole blood and for returning the recombined whole blood to the patient, an improved means for treating the plasma including an elongate chamber having an inlet and an outlet and a membrane within said chamber forming a vehicle having an immuno-adsorbent agent fixed thereon, said membrane being coiled in a spiral with each convolution of said spiral spaced from an adjacent convolution and being positioned within said chamber so that plasma flows through the space between the convolutions of said spiral coiled membrane.

Further according to the invention there is provided in an apparatus for use in the extracorporeal treatment of disease and of the type comprising means for withdrawing whole blood from a patient, means for separating plasma from the whole blood, means for treating the plasma including a chamber for receiving plasma and a vehicle positioned within the chamber and having an immuno-adsorbent agent fixed thereon which will interact and bond with an immunological reactant carried by the plasma that is passed through the chamber for removing the immunological reactant from the plasma, and means for recombining the substantially immunological reactant free plasma with the remainder of the whole blood and for returning the recombined whole blood to the patient, an improved means for treating plasma including a chamber, a vehicle within said chamber, and means within said chamber for establishing different flow rates of plasma through said chamber.

BRIEF DESCRIPTION OF THE DRAWINGS

FIG. 1 is a schematic block diagram of a fliud circuit of an apparatus for the extracorporeal treatment of disease.

FIG. 2 is a side view with portions broken away of a plasma treatment chamber adapted for use in the apparatus shown in FIG. 1 and constructed in accordance with the teachings of the present invention.

FIG. 3 is a sectional view taken along line 3—3 of FIG. 2.

FIG. 4 is a sectional view taken along line 4—4 of FIG. 2.

FIG. 5 is a perspective view of a spool situated within the chamber shown in FIG. 2 with a membrane thereon partially uncoiled.

FIG. 6 is a sectional view of another plasma treatment chamber adapted for use in the apparatus illustrated in FIG. 1 and constructed in accordance with the teachings of the present invention.

FIG. 7 is a sectional view taken along line 7—7 of FIG. 6.

FIG. 8 is an end view partially in section of the chamber shown in FIG. 6 and is taken along line 8—8 of FIG. 6.

FIG. 9 is an exploded perspective view of the plasma treatment chamber shown in FIG. 6.

DESCRIPTION OF THE PREFERRED EMBODIMENTS

Referring to the drawings in greater detail, in FIG. 1 there is illustrated a block schematic diagram of a fluid circuit of an apparatus 10 for the extracorporeal treatment of disease. As shown, the fluid circuit includes a first tubing 12 which is adapted to be coupled to a vein in one arm of a patient 14 by means of a hypodermic needle 16 which is injected into the one arm. For safety reasons, a fluid clamp 18 (shown schematically) is provided on the tubing 12. Also the first tubing 12 has associated therewith an electro-mechanically operated clamp 20 forming a first valve #1. The tubing 12 then has series coupled thereto an occluded vein monitor device 22 with an associated sensor 24. From the monitor device 22 the first tubing 12 extends over and forms part of a peristaltic pump 26 and is then series coupled to a high pressure monitor device 28 with an associated sensor 30. From the monitor device 28 the first tubing 12 extends into a centrifuge device 32 and to a bottom inlet 33 of a first compartment or receptacle 34 which is identified as a whole blood bag and which defines therein a separation chamber in which whole blood is separated into its components.

The receptacle 34 has a first outlet 36 at the center thereof adjacent a zone in the receptacle 34 where platelet rich plasma congregates. Receptacle 34 also has two outlets 40 and 42 at the upper corners thereof where red blood cells congregate. Outlet 36 provides not only an outlet for platelet rich plasma but also a return inlet for platelet rich plasma which is "contaminated" (mixed) with red blood cells when there is a spillover of red blood cells out of the first outlet 36.

The first outlet 36 of the first receptable 34 is coupled by a second tubing 44 to a loop 46 thereof located exterior of the centrifuge device 32 and which loop 46 extends about and forms part of a peristaltic pump 48. Also, positioned adjacent a light transmitting section of the loop 46 is a spill detector device 50 which includes an optical sensor for sensing a spillover of red blood cells mixed with platelet rich plasma flowing out of the outlet 36. More specifically, the device 50 includes a light emitting diode (LED), such as an infra-red LED sold by Texas Instruments under type No. TIL32 and a phototransistor, such as a phototransistor sold by Texas Instruments under type No. TIL81. The second tubing 44 then boes back into the centrifuge device 32 and is coupled to an inlet 52 of a second compartment or receptacle 55 which is identified as a platelet bag and which defines a chamber therein in which platelets are separated from plasma.

A third tubing 54 is connected to the outlets 40 and 42 of the receptacle 34 for returning the red blood cell rich fluid to the patient through a high/low pressure monitor device 56 with associated sensor 58 and an air bubble trap/filter 60 and associated air bubble sensor 62. As shown, the monitor device 56 and the filter 60 are coupled in series in the third tubing 54. Also another electro-mechanically operated clamp 64 is associated with a portion 66 of the tubing 54 coming out of the air bubble trap/filter 60 and defines a second valve #2. The sensor 62 can be optical or ultrasonic.

The end of the third tubing 54 is connected to a hypodermic needle 68 adapted for injection into the other arm of the patient 14, and, if desired for safety reasons, a fluid clamp 70 (shown schematically) can be provided on tubing 54 ahead of the needle 68.

The fluid circuit of the apparatus 10 also includes a container 72 of anticoagulant such as Acid Citrose Dextrose (ACD) which is coupled by a fourth tubing 74 extending about (and forming part of) the peristaltic pump 26 and past an electro-mechanically operated clamp 76 defining a third valve #3 to a junction 78 with the first tubing 12 between the needle 16 and valve #1. The container 72 is typically a flexible plastic container.

With this arrangement of the first tubing 12 and the fourth tubing 74 passing over the same peristaltic pump 26, the mixing of anticoagulant with whole blood and the withdrawing of whole blood from the patient is achieved essentially simultaneously. Also, the ratio of the cross-sectional area of the interior of the tubing 12 to the cross-sectional area of the interior of the tubing 74 is chosen to obtain a desired mixture of anticoagulant to whole blood. This ratio is preferably 8 to 1 thereby to obtain an 8 to 1 ratio of whole blood to anticoagulant.

The fluid circuit of the apparatus 10 further includes a container 80 of saline solution which is connected by means of a fifth tubing 82 through a drip chamber 84 and an electro-mechanically operated clamp 86 defining a fourth valve #4 to the first tubing 12 at a junction 88 between valve #1 and the occluded vein monitor device 22. The container 80 of saline solution is also coupled by means of a fifth tubing 90 through an electro-mechanically operated clamp 92 forming a fifth valve #5 to the top of the air bubble trap/filter 60. The container 80 is typically a flexible plastic container.

The pressure monitor devices 22, 28 and 56 each include a flow through chamber series connected in associated tubing 12 or 54, and an air filled closed chamber having a flexible diaphragm forming part of one wall of the flow through chamber and an outer wall which is situated adjacent the associated sensor 24, 30 or 58 which are pressure transducers and which sense changes in pressure on the outer wall.

It will be appreciated that platelets are removed from the plasma in the platelet separation bag 55 thereby to provide platelet poor, and essentially platelet free, plasma at an outlet 94 from the platelet bag 55.

The fluid circuit of the apparatus 10 of the present invention further includes a sixth tubing 96 which is connected from the outlet 94 of the platelet separation bag 55 to an inlet 97 to a plasma treatment chamber 98. A seventh tubing 100 extends from an outlet 101 from the plasma treatment chamber 98 to a junction 102 with the third tubing 54. At the junction 102 plasma which has been treated in the plasma treatment chamber 98 is recombined with the other blood components, namely red blood cells.

A plasma bypass arrangement 104 is provided for recombining the separated platelets with the other blood components. The bypass arrangement 104 includes a bypass tubing 105 between tubings 96 and 100, an electro-mechanically operated clamp 106 forming a sixth valve #6 associated with tubing 96 ahead of the plasma bypass tubing 105, an electro-mechanically operated clamp 108 defining a seventh valve #7 associated with the tubing 100 before it connects with the bypass tubing 105 and an electro-mechanically operated clamp 112 defining an eighth valve #8 associated with the plasma bypass tubing 105. Valves #6 and #7 are open and valve #8 is closed during treatment of the plasma.

In the operation of the plasma bypass arrangement 104, valves #6 and #7 are closed and valve #8 is opened so that platelet rich plasma can be passed directly from tubing 96 to tubing 100 for recombination of the cellular components of the blood and the plasma at the junction 102.

Although not shown in FIG. 1, it will be understood that the plasma treatment chamber 98 has a suitable vehicle therein to which is fixed a specific immunoadsorbent agent for interacting and bonding with a specific immunological reactant in the plasma to remove such immunological reactant from the plasma.

The operation of the apparatus 10 for processing whole blood through the fluid circuit and for treating the plasma separated from the whole blood will now be described briefly with reference to FIG. 1.

Valve #1 is first opened to allow saline to purge the input needle 16 prior to injection in the patient 14. Then valves #1, #3, #5 and #8 are closed. Valves #2, #4, #6 and #7 are open.

Then, saline is pumped by the first pump 26 through the fluid circuit of the apparatus 10 until no more air bubbles are sensed by the air bubble sensor 62, i.e., until saline is sensed. Next, the second pump 48 is started and saline is pumped through the platelet receptacle 55. Since the centrifuge device 32 is not running at this time, the receptacles 34 and 55 are not filled to capacity. Air is expelled through the needle 68.

After a short time, e.g., one to five minutes, the platelet receptacle/bag 55 will be filled, all air expelled and saline fills the entire system, i.e., the fluid circuit of the apparatus 10 up to valve #2. When saline is sensed by detector 62, valve #2 is closed and valve #5 is opened. After a period of recirculation of saline, pumps 26 and 48 are stopped and valve #2 is opened.

Parenthetically, during this priming operation, the air bubble sensor 62 is checked when air bubbles are flowing through the air bubble trap/filter 60 to make sure that sensor 62 is working properly and then later, sensor 62 is checked to make sure there are no more bubbles after the system is filled with saline.

Now two venipunctures are made with the needles 16 and 68 to insert the needles 16 and 68 into the arms of the patient 14, and valves #1, #3, #5, #6 and #7 are open and valves #2 and #8 are closed.

With the needles 16 and 68 connected to the veins of a patient and the system full of saline, the pumps 26 and 48 are started and whole blood is pumped into the system and into the centrifuge device 32.

It will be noted that the tubings 12, 44 and 54 extending into the centrifuge device 32 may be combined in an umbilicus which is rotated at a speed ½ the speed of the centrifuge device so that twisting is avoided and no fluid seals are required. This arrangement and operation of the centrifuge device 32 is more fully described in a co-pending application Ser. No. 657,187 filed Feb. 11, 1976 and entitled: CENTRIFUGAL LIQUID PROCESSING APPARATUS.

When approximately 120 milliliters of whole blood has been pumped into the fluid circuit of the apparatus 10, most of the saline solution will have been pumped back into the container 80. Valve #2 is now opened so that processed blood fluid mixed with some saline solution can now be returned to the patient.

After starting pumps 26 and 48 no further operator attention is required until the plasma treatment run has been completed and the operator is ready to return the recombined blood components to the patient. Also, during the run, the spillover detector 50 operates the pumps 26 and 48 in such a manner as to prevent red blood cell contamination of the plasma being withdrawn from receptacle 34. The manner in which this is accomplished is explained in more detail in a co-pending application Ser. No. 843,222 filed Oct. 18, 1977 and entitled: METHOD AND APPARATUS FOR PROCESSING BLOOD wherein an apparatus similar to apparatus 10 is disclosed.

Typically, the whole blood is withdrawn from the patient at a volumetric rate of between 15 and 50 milliliters per minute and through empirical tests it has been found that a whole blood rate of withdrawal of approximately 30±5 milliliters per minute provides good results. Accordingly, the rate of withdrawal, i.e., the speed of the peristaltic pump 20 is started at a rate of 26 milliliters per minute.

As the whole blood is being drawn into the first separation chamber or receptacle 34, the centrifugal force acting on the receptacle 34 causes separation of the components of the whole blood. Platelet rich plasma congregates in a zone at the top of the receptacle 34 adjacent to the outlet 36 and red blood cells congregate at the upper corners of the receptacle 34 adjacent outlets 40 and 42. This is achieved by the particular construction and orientation of the receptacle 34 which is described in more detail in a co-pending application Ser. No. 843,296 filed Oct. 18, 1977 and entitled: CENTRIFUGAL LIQUID PROCESSING SYSTEM.

The centrifuge device can be rotated at any one of several speeds of rotation from 0 to 1600 RPM. In a working example of the apparatus 10, a speed of 1400 RPM has been found to work very well. The speed of rotation of the centrifuge device 32 must be, of course, correlated with the distance of the two receptacles 34 and 55 from the axis of rotation of the centrifuge device 32 in order to obtain a desired "g" force on the blood fluid in the respective receptacles 34 and 55. In this respect, it has been found that a "g" force of between 150 and 600 "g's" provides good results, that is to say, a good separation of blood into its components. In a working example of the apparatus 10, the centrifuging takes place in the first and second receptacles 34 and 55 at approximately 285 "g's".

In the processing of whole blood it has been found best to process about 3 liters of blood at any one time. Accordingly, the controls for the apparatus 10 are set to process 3 liters of whole blood from the patient.

In light of the texture, size and number of particles in the blood, namely, red blood cells, white blood cells and platelets, whole blood does not strictly obey the various physical chemistry and fluid dynamic laws. Accordingly, the various operating parameters described herein have been determined more or less empirically. In this respect, it has been found that the efficiency of separation of plasma rich in platelets, referred to as platelet rich plasma from the remainder of the whole blood in the receptacle 34 begins at a point when the hematocrit of the red blood cell rich blood fluid out of the outlets 40 and 42 from receptacle 34 (hereinafter "hematocrit out") is approximately 56. Then, essentially 50% effectiveness of separation is obtained when the hematocrit out is 63. Finally, close to 100% effective and efficient separation of platelet rich plasma from the whole blood occurs when the hematocrit out is roughly 71.

With this relationship determined empirically, 285 "g's" on the first and second receptacles 34 and 55, provides a hematocrit out of approximately 70 and efficient separation of platelet rich plasma from whole blood.

During the operation of the apparatus 10 in separating plasma from whole blood and passing it through the plasma treatment chamber 98, a specific immunoadsorbent agent within the chamber 98 removes a specific immunological reactant from the plasma. In this way and as described above, the blood of the patient is treated to remove a substance therefrom which is harmful to the body because of a particular disease existing in the body or because of a particular condition of the body. In this way the body's own immune system is better enabled to heal the body and allow the body to heal itself.

After a sufficient quantity of blood has been treated to remove a specific immunological reactant, the centrifuge device 32 is stopped and the pumps 26 and 48 are allowed to continue running so that platelets can be flushed by plasma from the platelet separation bag 55. At this time, valves #6 and #7 are closed and valve #8 is opened to bypass platelet rich plasma around the plasma treatment chamber 98 and to the junction 102.

When the spill detector 50 detects red blood cells mixed with the plasma the pumps 26 and 48 are stopped, valves #1 and #2 are closed and valve #4 is opened. Then pumps 26 and 48 are operated and saline is pumped into the fluid circuit for a predetermined period of time to flush cellular blood components and plasma from the fluid circuit and to junction 102 where they are recombined. From there, the recombined blood passes through the air bubble trap/filter 60 and back into the patient 14. When a quantity of saline sufficient to fill the fluid circuit from junction 88 to valve 64 has been pumped into the fluid circuit, valves #3 and #4 are closed and valve #5 is opened. At this time the apparatus 10 can be stopped and the hypodermic needles 16 and 68 can be removed from the patient 14.

Except for the plasma treatment chamber 98, the apparatus 10 as described above is similar to an apparatus disclosed in a co-pending application Ser. No. 843,222 filed Oct. 18, 1977 and entitled: METHOD AND APPARATUS FOR PROCESSING BLOOD. Also, according to the teachings of the present invention the plasma treatment chamber 98 can take various forms which enhance the treatment of the plasma passed therethrough.

Referring now to FIGS. 2-5 there is illustrated therein one form of plasma treatment chamber generally identified by the reference numeral 198. This plasma treatment chamber 198 includes a hollow cylinder 200 having a closed end 202 except for an outlet opening 204 therethrough. The other end is open and has an annular end flange 206 to which is secured an end cap 208 which has an inlet opening 210 therethrough. The end cap 208 is secured by four fasteners 212 to the flange 206 with sealing being provided by an O-ring 214. It will be understood that tubing 96 will be connected to inlet opening 210 and tubing 100 will be connected to outlet opening 204.

In accordance with the teachings of the present invention a spool 216, best shown in FIG. 5, is received within the hollow cylinder 200 and has a membrane 218 wound around a spindle or core member 220 of the spool 216. Also, end flanges 222 and 224 are secured to opposite ends of the spindle 220 and define end hubs of the spool 216.

As best shown in FIGS. 2, 3, and 5, the membrane 218 has a plurality of elongate spacers 226 secured to one side surface 228 thereof in parallel spaced relationship along the length of the membrane when it is unraveled from the spool 216. Each elongate spacing member 226 extends from one side of the unraveled membrane 218 forming one end of the coiled membrane 218 to the other side which forms the other end of the coiled membrane. By means of the spacers 226 the membrane 218, when coiled on the spool 216, forms a spiral coil with spaces provided between adjacent spacers 226 and between adjacent convolutions of the spiral coiled membrane 218 to facilitate axial flow of plasma through the coiled membrane.

Further to facilitate axial flow of plasma through the coiled membrane 218, each of the end flanges 222 and 224 has a plurality of radial slots 232 and 234 formed therein for permitting plasma to pass through the end flange 222 to enter the spaces between convolutions of the membrane 218 and to flow axially of the spiral coiled membrane 218 to and through end flange 224 and thereby through the plasma treatment chamber 198. While the plasma is flowing through the spaces between each adjacent pair of spacers 226 and the convolutions of the spiral coiled membrane 218, an immunological reactant in the plasma will interact and bond with an immuno-adsorbent agent on the membrane 218 thereby to remove a substantial portion, if not all, of the immunological reactant from the plasma.

Referring now to FIGS. 6-9, there is illustrated therein another plasma treatment chamber which is constructed in accordance with the teachings of the present invention and which is generally identified by reference numeral 298. As best shown in FIGS. 6 and 9, the plasma treatment chamber 298 includes a hollow cylinder 300 closed off at one end 302 but for an outlet opening 304 therethrough. The other end of the cylinder 300 is open and has an annular end flange 306 to which an end cap 308 with an inlet opening 310 therethrough is attached by four fasteners 312. Nylon microspheres or beads, which are shown enlarged in FIG. 6 and which are generally identified by reference numeral 314, are situated within the cylinder 300 and define a vehicle to which is bound an immuno-adsorbent agent by known techniques. Other particles, of course, can be used for the vehicle.

According to the teachings of the present invention, it is believed that increased adsorbance of an immunological reactant by the immuno-adsorbent agent on the nylon beads 314 can be enhanced by causing increased circulation of the plasma past the beads 314. To achieve this end, different flow rates are established within the cylinder 300 thereby to cause plasma flow, which may be turbulent, around and past the beads 314. To achieve different flow rates at different locations within the chamber, a cone 316 is situated in the cylinder 300 with a base 318 of the cone 316 situated adjacent the inlet opening 312 and an apex 320 of the cone 316 extending toward outlet opening 304.

The base 318 of the cone 316 is threaded onto a base member 324 which has three pins 326 extending therefrom which are received in mating holes in the end cap 308 for locating and mounting the base member 324 and cone 316 as illustrated in FIG. 6. An inlet screen 330 is mounted between the base 318 of the cone 316 and the base member 324 and between the end cap 308 and the annular flange 306. An outlet screen is mounted in the cylinder 300 over the outlet opening 304.

As shown, plasma flows into the chamber 298 through the inlet 312, around the bottom of the base member 324 and around the pins 326, through an annular area defined around the base member 324 and the interior wall of the end cap 308, through the screen 330 and along the cone 316 toward the apex 320 of the cone 316 and through the nylon beads 314 to the outlet opening 304. From there the plasma flows through the screen 332 and through the outlet 304 from the plasma treatment chamber 298.

It will be appreciated that the cross-sectional areas through which the plasma flows as it flows through the chamber 298 increases as the plasma travels along the length of the cone 316 and toward the apex 320 of the cone 316. As a result, different flow rates and pressures are established along the flow path of the plasma along the length of the cone 316 thereby, it is believed, to create turbulence within the plasma treatment chamber 298.

From the foregoing description it will be apparent that the plasma treatment chambers 98, 198, and 298 for the apparatus 10 for the extracorporeal treatment of disease of the present invention have a number of advantages some of which have been described above and others of which are inherent in the invention. Accordingly, the scope of the invention is only to be limited as necessitated by the accompanying claims.

We claim:

1. In an apparatus for the extracorporeal treatment of disease and of the type comprising means for withdrawing whole blood from a patient, means for separating plasma from the whole blood, means for treating the plasma including a chamber for receiving the plasma and a vehicle positioned within the chamber and having an immuno-adsorbent agent fixed thereon which will interact and bond with an immunological reactant carried by the plasma that is passed through the chamber for removing the immunological reactant from the plasma, and means for recombining the substantially immunological reactant free plasma with the remainder of the whole blood and for returning the recombined whole blood to the patient, an improved means for treating the plasma including an elongate chamber having an inlet and an outlet and a membrane within said chamber forming a vehicle having an immuno-adsorbent agent fixed thereon said membrane being coiled in a spiral with each convolution of said spiral spaced from an adjacent convolution and being positioned within said chamber so that plasma flows through the space between the convolutions of said spiral coiled membrane.

2. The apparatus according to claim 1 including a plurality of elongate spacers which are attached to one side of said membrane and which extend from one side edge forming part of one end of said coiled membrane to the other side edge of said membrane forming part of the other end of said coiled membrane, said elongate spacers being spaced apart along the length of the uncoiled membrane and serving to space one convolution from the adjacent convolution of said spiral coiled membrane.

3. The apparatus according to claim 1 including a core member on which said membrane is coiled in a spiral.

4. The apparatus according to claim 3 including a circular end flange mounted on each end of said core member to form a spool on which the convolutions of said spiral coiled membrane are situated, each flange having passage means therethrough for allowing plasma to pass through said flange.

5. The apparatus according to claim 4 wherein said passage means in each circular end flange are defined by radially extending slots in said flange.

6. The apparatus according to claim 1 wherein said chamber includes a cylindrical, elongate chamber substantially closed at one end except for said outlet therein and being open at the other end and an end cap releasably fixed to and closing off said open other end and having said inlet therethrough.

7. In an apparatus for use in the extracorporeal treatment of disease and of the type comprising means for withdrawing whole blood from a patient, means for separating plasma from the whole blood, means for treating the plasma including a chamber for receiving plasma and a vehicle positioned within the chamber and having an immunoadsorbent agent fixed thereon which will interact and bond with an immunological reactant carried by the plasma that is passed through the chamber for removing the immunological reactant from the plasma, and means for recombining the substantially immunological reactant free plasma with the remainder of the whole blood and for returning the recombined whole blood to the patient, an improved means for treating plasma including a chamber, a vehicle within said chamber, and means within said chamber for establishing different flow rates of plasma through said chamber.

8. The apparatus according to claim 7 wherein said vehicle is defined by particles having a large surface area and having an immunoadsorbent agent bonded thereto and said means for establishing different flow rates within said chamber includes a cone disposed within said chamber, said particles being disposed within said chamber around said cone.

9. The apparatus according to claim 8 wherein said chamber is elongate, is closed at one end except for an outlet therethrough and is open at the other end, and wherein said said chamber includes an end cap secured to said other end of said chamber for closing said open other end and having an inlet therethrough, the base of said cone being mounted to said end cap, and passage means for allowing plasma to flow from said inlet around said base of said cone and along and toward the apex of said cone situated within said elongate chamber.

* * * * *